United States Patent [19]

Jensen et al.

[11] Patent Number: 5,534,562
[45] Date of Patent: Jul. 9, 1996

[54] COMPOSITIONS AND METHODS FOR PRIMING AND SEALING DENTAL AND BIOLOGICAL SUBSTRATES

[75] Inventors: Steven D. Jensen, Sandy; Dan E. Fischer, Midvale, both of Utah

[73] Assignee: Ultradent Products, Inc., South Jordan, Utah

[21] Appl. No.: 418,764

[22] Filed: Apr. 7, 1995

[51] Int. Cl.$^6$ .................. C08K 5/10; A61K 6/08; A61C 5/00; A61C 5/04

[52] U.S. Cl. .................. 523/118; 523/115; 523/116; 524/379; 433/217.1; 433/226; 433/228.1

[58] Field of Search .................. 523/116, 118, 523/115; 524/379; 433/228.1, 226, 217.1

[56] References Cited

U.S. PATENT DOCUMENTS

| | | | |
|---|---|---|---|
| 4,155,890 | 5/1979 | Hofacker-Freifrau | 260/23 AR |
| 4,225,476 | 9/1980 | Hammer et al. | 260/27 R |
| 4,362,510 | 12/1982 | Brauer et al. | 433/199 |
| 4,362,842 | 12/1982 | Masuhara et al. | 524/854 |
| 4,486,179 | 12/1984 | Brauer et al. | 433/199 |
| 4,514,342 | 4/1985 | Billington et al. | 260/952 |
| 4,542,168 | 9/1985 | Chang et al. | 523/118 |
| 4,657,941 | 4/1987 | Blackwell et al. | 522/14 |
| 4,711,913 | 12/1987 | Tateosian et al. | 522/14 |
| 4,759,798 | 7/1988 | von Nostitz | 106/35 |
| 4,806,381 | 2/1989 | Engelbrecht et al. | 427/2 |
| 4,830,616 | 5/1989 | Okuda et al. | 433/217.1 |
| 4,880,660 | 11/1989 | Aasen et al. | 427/2 |
| 4,950,697 | 8/1990 | Chang et al. | 523/116 |
| 4,966,934 | 10/1990 | Huang et al. | 524/315 |
| 4,986,754 | 1/1991 | Chang et al. | 433/224 |
| 5,147,903 | 9/1992 | Podszun et al. | 523/115 |
| 5,154,762 | 10/1992 | Mitra et al. | 106/35 |
| 5,158,825 | 10/1992 | Altwirth | 428/286 |
| 5,178,870 | 1/1993 | Schaeken et al. | 424/405 |
| 5,192,802 | 3/1993 | Rencher | 514/535 |
| 5,252,629 | 10/1993 | Imai et al. | 523/118 |
| 5,264,485 | 11/1993 | Müller | 524/724 |
| 5,264,513 | 11/1993 | Ikemura et al. | 526/318 |
| 5,276,068 | 1/1994 | Waknine | 522/28 |

OTHER PUBLICATIONS

Baba, et al., Abstract of *Selective Inhibition of Human Immunodeficiency Virus Type 1 Replication by Novel Fluoroalkylated Oligomers in Vitro*, Fukushima Medical College, Department of Microbiology, 24–30 (Jan. 1994).

Bean, et al., Abstract of *Effect of Esterase on Methacrylates and Methacrylate Polymers in an Enzyme Simulator for Biodurability and Biocompatibility Testing*, University of Missouri, School of Pharmacy, Kansas City, Kansas, 59–63 (Jan. 1994).

Lee, Abstract of *Constant–rate Drug Release From Novel Anionic Gel Beads with Transient Composite Structure*, Department of Chemical Engineering and Applied Chemistry, University of Toronto, 964–7 (Sep. 1993).

Van Meerbek, et al., *Morphological Aspects of the Resin–Dentin Interdiffusion Zone with Different Dentin Adhesive Systems*, Department of Operative Dentistry and Dental Materials, Katholike Universiteit te Leuvae (Feb. 24, 1992).

Wu et al., Abstract of *Expression of Integrin and Organization of F–actin in Epithelil Cells Depends on the Underlying Surface*, Boston University School of Medicine, Boston, Mass., 878–890 (Mar. 1994).

Balsam Canada, Merck Index, 137 (10th ed. 1983).

Methacrylic Acid, Merck Index, 850 (10th ed. 1983).

*Primary Examiner*—Paul R. Michl
*Assistant Examiner*—LaVonda R. DeWitt
*Attorney, Agent, or Firm*—Workman Nydegger Seeley

[57] ABSTRACT

Compositions and methods for priming or sealing dental or biological substrates for subsequent bonding. The primer is particularly useful for priming dentin of a tooth to prepare the dentin for bonding with a resinous material. The primer comprises a mixture of a polymerization initiator such as camphoroquinone and a polymerizable promoter such as methacrylic acid. Polymerizable promoters within the scope of the present invention have at least one ethylenically unsaturated group and at least one carboxylic acid group. The primer may further comprise a solvent such as ethanol, a natural resin such as Canadian balsam and a polymerizable resin such as 2-hydroxyethyl methacrylate (HEMA). The primer can also be formed from a mixture of a polymerization initiator, a natural resin and a polymerizable resin.

108 Claims, No Drawings

COMPOSITIONS AND METHODS FOR PRIMING AND SEALING DENTAL AND BIOLOGICAL SUBSTRATES

BACKGROUND OF THE INVENTION

1. The Field of the Invention

This invention relates to improved compositions and methods for priming or sealing dental substrates and biological substrates, particularly exposed dentinal tooth surfaces, in order to obtain strong adhesion when followed by an appropriate material such as a resinous material or glass ionomer cement. More specifically, the invention relates to improved compositions and procedures for applying an approximately pH neutral dentin primer requiring no mixing by the applicator as it is a highly stable one component primer system.

2. The Prior State of the Art

Resinous materials are widely used for a variety of dental uses, including cavity filling, cosmetic enhancement and the cementation or adhesion of resinous and non-resinous materials.

Because tooth enamel is comprised mostly of calcified minerals, it is very hard and can be physically cleaned and chemically etched (conditioned) in preparation for bonding with resinous materials. Once dried by air, and/or using a drying agent, the enamel tends to remain relatively dry. After the enamel has dried, hydrophobic type resins can be bonded on to the enamel. This bond between dried enamel and hydrophobic resins as well as the process of obtaining such bonds are possible primarily due to the inorganic mineral content of enamel which is very high compared to that of dentin.

In sharp contrast to the process involved in bonding resinous materials to enamel, it is much more difficult to obtain completely dry dentin by using a drying agent and/or air drying techniques. This is because dentin contains thousands of dentin tubules which radiate outward from the pulp of the tooth and which contain pulp fluid under pressure. A cross-section of dentin contains approximately 35,000 dentin tubules per square millimeter, which can ooze fluids from the pulp after the dentin surface is cut or drilled and the smear layer has been altered or removed.

Cutting or drilling the dentin creates a "smear layer," which is a semi-attached, weakened layer of dentin. Tests have shown that it is difficult to obtain strong bonds between resinous materials and dentin unless the smear layer has been substantially removed. This is usually accomplished by the use of aqueous acid solutions or chelating agents.

Another obstacle to obtaining strong bonds between resinous materials and dentin is that dentin is relatively soft and less durable than enamel. While enamel has a mineral content over 97% comprising mainly calcium hydroxyapatite, phosphates, etc, dentin comprises only about 45% mineral material—the other 55% being a fibrous protein matrix and water. Dentin, therefore, has a hardness, strength and chemical composition more similar to bone tissue.

Not only is enamel easier to dry and to keep dry compared to dentin, it can be more predictably etched in order to yield a superior bonding surface. Chemical etching, typically by means of a moderately strong acid (such as 30–40% aqueous phosphoric acid) creates microscopic irregularities and undercuts into which a resinous material can enter, thereby providing a strong, reliable bond to the etched enamel.

The first attempts to improve dentin bonding involved trying to implant resinous "tags" within the cores of the dentin tubules. This mechanism, developed by Japanese scientists in the 1970's, postulated that resinous materials could form reliable bonds via these tags. However, due to the relatively small cross-sectional area of the dentin tubules compared to the dentin surface, and because resins shrink upon polymerizing, and due to the pulp fluid within the dentinal tubules, the resinous tags did not adhere well to the dentin. Hence, this method did not result in acceptably strong and durable bonding to dentin.

During this time and after, the theory among dentists and dental researchers in the U.S. was that it was not desirable to remove the entire smear layer, although it later became understood that any resulting bonds could be no stronger than the bond of the smear layer to the dentin.

Later generation formulations generally reflect the teachings of Rafael L. Bowen and others. These achieve bond strengths of around 14–20 MPa. A number of patents generally reflect this later school of thought, including, e.g., U.S. Pat. No. 4,588,756 to Bowen; U.S. Pat. No. 4,659,751 to Bowen; and U.S. Pat. No. 4,964,911 to Ibsen et al. Bowen '756 teaches a three step process which includes the following steps: first, applying a polyprotic acid; second, applying a solvent containing at least one compound selected from the group consisting of N-phenylglycine, the adduct of N(p-tolyl)glycine, and glycidyl meth-acrylate (hereinafter "NPG-GMA"), and the addition reaction product of N-phenylglycine and glycidyl methacrylate (hereinafter "NPG-GMA"); and third, applying a solution containing at least one compound selected from the group consisting of the addition reaction product of pyromellitic acid dianhydride and two hydroxyethyl methacrylate (hereinafter "PMDM"), the addition reaction product of 3,3',4,4'-benzophenonetetracarboxylic dianhydride and 2-hydroxyethylmethacrylate (hereinafter "BTDA-HEMA") and 4-methacryloxyethyl-trimelliticanhydride (hereinafter "4-META").

Bowen '751 teaches a two step process which includes the following steps: first, applying an aqueous acid solution including strong acids, acids containing polyvalent cations, and acids which form precipitates with calcium, and a compound selected from the group consisting of N-phenylglycine, NTG-GMA, and NPG-GMA; and second, applying a solution containing either PMDM, BTDA-HEMA or 4-META.

Ibsen '911 teaches a similar three step process which includes the following steps: first, applying an acidic solution containing a variety of strong and polyprotic acids; second, applying a solvent containing a variety of different resins or amino acids; and third, applying a solution of PMDM.

A number of these later generation commercial dentin bonding agents are sold, including All Bond II (manufactured by Bisco Dental Products), Prisma Universal Bond III (manufactured by Dentaply), Tenure (manufactured by Den-Mat Co.), and Multi-Purpose (manufactured by 3M).

Dentin primers are now available which do not require mixing, such as, Opti-Bond from Kerr and Prime and Bond from Caulk Dentsply. Although, such primers and/or bonding agents can be more quickly used than primers requiring mixing at the time of application, there are disadvantages which minimize their usefulness. One of the primary disadvantages of these primers is related to the need for multiple coats. The efficiency gained by using premixed primers is lost by the need for multiple coats to obtain adequate coverage and polymerization. The economic usefulness of the primers is also limited since the shelf life of such dentin primers is typically very short despite the claims of the manufacturers. It is well known in the industry among prominent lecturers and clinicians that most of the primers have a significantly shorter shelf life than claimed by the manufacturers. Additional problems may result from the highly acidic nature of such primers. The low pH is potentially harmful since the polymerized primer may leach and since a residual portion of the primer is typically not polymerized thereby remaining acidic and in close contact with the dentin. A residual unpolymerized portion could also potentially cause continued degradation to the remaining tooth structure. Low ph may also cause potentially high tooth sensitivity and may even cause painful injury if the acidic primer comes into contact with the pulp of a tooth underlying the exposed dentin.

Additionally conventional primers when applied to a biological substrate as a sealant before application of cementation materials such as glass ionomer cement, polycarboxylates and the like usually to interfere with the ability of cements to bond. Inadequate bonding strengths usually result when a conventional primer is applied to a metal, enamel, porcelain or composite and then followed by a bonding resin.

In view of the foregoing, it would be an advancement in the dental art to provide compositions and methods for more efficiently obtaining stronger, more predictable bonds between dentin and subsequently placed resinous materials. It will be appreciated that it would also be a significant improvement over the prior art to provide dental compositions having a long shelf life which would result in dependable bonds over time during storage and usage Further, it would be a significant improvement if the dentin bonding primer was stable as one component and more stable than all types of existing dentin primers.

It would be an improvement over the prior art to provide compositions and methods for sealing a biological substrate without interfering with the bond achieved with a material which is thereafter applied such as glass ionomer cement, carboxylate cements or the like.

Further, it would be a significant advancement in the dental art to provide composition and methods for a single component primer which has an approximately neutral pH level.

Finally, it would be an important advancement if such compositions and methods could provide significant bonding strengths to an appropriately conditioned enamel, porcelain, metal or composite surface(s) when followed by an appropriate resin.

Such compositions and procedures for achieving these results are set forth and claimed herein.

SUMMARY AND OBJECTS OF THE INVENTION

The present invention provides compositions and methods for priming or sealing dentin of a tooth to prepare the dentin for bonding with an appropriate resinous material. Additionally, the primer can be used with other dental or biological substrates such as enamel, porcelain or composite crowns, and metal crowns or fillings. The resulting bonds have been shown to be more durable over time. The compositions and methods of the present invention also allow for greater convenience because they remain stable until needed by the dentist over a significantly long shelf life.

In a preferred embodiment, the dentinal smear layer is first removed by conditioning the dentin surface with 35% phosphoric acid, after which the dentin is washed with water to remove the aqueous acid and dissolved dentin minerals. Although 35% aqueous phosphoric acid is preferred, concentration ranging from 10% to 40% works well. In addition, other dilute acids or chelators also work well. After the conditioning treatment, surface water is removed by air.

The dentin primer of the present invention is applied to the dentin after appropriate water removal. The dentin primer is applied to seal the dentinal tubules and prepare the dentin surface for bonding with an appropriate resinous material.

The dentin primer comprises at least one polymerizable component and at least one polymerization initiator. In one embodiment of the present invention, the dentin primer comprises a mixture of a polymerization initiator, such as camphoroquinone, and a polymerizable promoter, such as methacrylic acid. Polymerizable promoters within the scope of the present invention have at least one ethylenically unsaturated group and at least one carboxylic acid group. The dentin primer may further comprise a volatile solvent such as ethanol, a natural resin such as Canadian balsam, or a polymerizable resin such as HEMA. In another embodiment, the dentin primer is formed from a mixture of a polymerization initiator, a natural resin and a polymerizable resin. The preferred embodiment of the dentin primer comprises methacrylic acid, HEMA, Canadian balsam, ethanol and camphoroquinone.

An advantage of the present invention is that the dentin primer of the present invention is stable over time.

Although, patents may claim high bond strengths, hypothetical bond strengths obtained by applying the prior art bonding agents under ideal conditions are of little worth if the exigencies and difficulties of actual dental work make it impossible to repeat the process under actual conditions encountered by the dentist or if the shelf life is so short that testing conditions using fresh material are not comparable to the time implications of how they are used in a typical dental office.

In addition to the above the benefits, the one component primer system of the present invention requires no mixing by the applicator. This one component primer system has an approximately neutral pH level and is adequately integrated into the conditioned dentin with one application.

Yet another advantage of the present invention is ability of the compositions to be applied as a sealant to a biological substrate without decreasing the bond strength of a material applied thereafter such as glass ionomer cement or polycarboxylate cement. The present invention also yields adequate bonding strengths when applied to an appropriately conditioned enamel, porcelain, metal or composite and then followed by a bonding resin.

From the foregoing, it will be appreciated that an object of the present invention is the development of dental compositions and methods for more efficiently obtaining stronger, more predictable bonds between dentin and subsequently placed resinous materials. It will also be appreciated that an object of the present invention is to provide compositions having a long shelf life which would result in dependable bonds over time during storage and usage.

Another object of the present invention is the development of dental compositions and methods which are more simple to use than in the prior art by providing a dentin primer which is stable as a one component system and more stable than all types of existing dentin primers.

Another feature and object of the present invention is to provide compositions and methods for sealing a biological substrate without interfering with the bond achieved with a material which is thereafter applied such as glass ionomer cement or polycarboxylate cements.

Yet another object of the present invention is the development of compositions and methods for a single component primer which has an approximately neutral pH level.

Finally, an object of the present invention is the development of compositions and methods that can provide significant bonding strengths to an appropriately conditioned enamel, porcelain, metal or composite surface(s) when followed by an appropriate bonding resin.

Those and other objects and features of the present invention will become more fully apparent from the following description and appended claims, or may be learned by the practice of the invention.

DETAILED DESCRIPTION OF THE PREFERRED EMBODIMENTS

The present invention relates to compositions and methods for priming or sealing a substrate in a living body including prosthetic substrates to be incorporated into the living body, such as a dental or biological substrate, in order to obtain strong adhesion when followed by an appropriate material such as a resinous material or glass ionomer cement. The term "dental substrate" as used in the specification and the appended claims is defined to include tooth enamel, dentin, other structures of a tooth, metal crowns or fillings, porcelain crowns, composite fillings or crowns, other dental prosthesis and other materials related to the repair and reconditioning of teeth. The term "biological substrate" as used in the specification and the appended claims is defined as an organic or inorganic body part of a living organism. Examples of biological substrates include but are not limited to bone, fingernails and also some dental substrates such as enamel and dentin. The present invention has been developed particularly for use in priming dentin for bonding or for use in sealing dentin, however, one skilled in the art can use the teachings as applied to dentin for use in priming for bonding or sealing other substrates in a living body in addition to dentin, particularly dental and biological substrates.

The dental and biological substrates can also be conditioned before the primer composition is applied, although, it is not always necessary to condition the substrate. Conditioning dental and biological substrates, such as dentin and enamel, generally involves application of an acid such as phosphoric acid. Porcelain is also typically conditioned with an acid or grit blasting treatment, hydrofluoric acid is particularly effective. Metals are typically conditioned by grit blasting. The present invention includes a kit comprising a substrate conditioner such as an aqueous acid solution, a primer and an appropriate bonding resin.

The present invention is particularly useful for priming exposed dentinal tooth surfaces. After the primer has been applied to the dentin, an appropriate resinous material can be bonded to the primer. Additionally, the present invention can be used to seal dentin before a cement is applied such as glass ionomer cement, polycarboxylate cements (polyacrylic acid formulations) and the like without negatively effecting the bond formed by the cement. An increase in bond strength results from priming such a surface before applying the glass ionomer cement, which is a surprising result. It is surprising that the bond is strengthened since conventional primers tend to interfere with bonds formed by glass ionomer cements to dentin.

Dentin contains an enormous number of dentin tubules that radiate outwardly from the pulp chamber. These dentinal tubules are filled with a fluid which is contiguous with the pulp chamber. Although the drilling and cutting of enamel is relatively painless, fluid movement through the dentinal tubules can act like nerves and can induce pain.

Once the dentin is cut, internal pressure within the pulp chamber can cause the fluid within the dentinal tubules to flow out of the tubules and onto the dentinal surface. This has created one of the major obstacles to obtaining strong bonds to dentin. The cutting of dentin by means of a high speed drill or other cutting devices, as are typically employed by dentists to clear away tooth decay and shape dimensions for the restoration, causes the formation of a weakened, semi-attached layer which remains over the dentin called the smear layer. The smear layer has been a major obstacle to obtaining strong bonds between resinous materials and dentin.

In addition, mucous-like fluid from the pulp chamber oozes through the dentin tubules and deposits itself on the smear layer and is not easily dried. Therefore, it is advantageous to remove and/or alter the entire smear layer. Then, before the dental material is applied, it is important to seal the dentin tubules to provide a bonding substrate and to prevent fluid movement in the dentin tubules thus alleviating sensitivity.

A preferred method entails first contacting the dentin surface with an aqueous acid solution for about 20 seconds in order to remove substantially all of the smear layer, but without damaging the dentin itself. It has been found that aqueous phosphoric acid works well in conditioning the dentin. Any conventional conditioner can be used within the scope of the present invention to condition the dentin including acidic solutions such as aqueous citric acid, nitric acid, and other acids, as well as other known dentin conditioners including chelators.

The phosphoric acid solution within the scope of the present invention will typically have a concentration within the range from between about 10% to about 40% (weight to volume), with a concentration of about 35% being the most preferable. A phosphoric acid solution having a concentration of 35% (weight to volume) is available from Ultradent Products, Inc. in Salt Lake City, Utah, under the trademark Ultraetch®. After the smear layer is removed by the acid solution, any excess acid is removed by flushing the etched dentin with water.

Once the smear layer has been substantially removed, the second step entails removing any excess moisture from the dentin surface. This is preferably performed by means of air blowing or use of absorbent materials.

After the excess water has been removed from the dentin, the third step involves applying the dentin primer to prepare the dentin surface for bonding. This is accomplished by applying the premixed bonding agent of the present invention. After the dentin primer is applied, the application is blown with clean air to thin the primer and/or dry solvent from the primer. Appropriate resinous materials can be applied to the dentin after polymerization has occurred. An appropriate resin material is applied to the dentin after polymerization of the primer. Appropriate resins will usually include HEMA, Bis-GMA, urethane dimethacrylate "CUDMA"), TEGDMA or a combination of these.

The primer of the present invention comprises at least one polymerization initiator and at least one polymerizable component. In one embodiment of the present invention, the polymerizable component is a polymerizable promoter. The term "polymerizable promoter" as used in the specification and the appended claims refers to a polymerizable monomer or prepolymer having at least one ethylenically unsaturated group and at least one carboxylic acid group, the polymerizable promoter is characterized as being capable of being polymerized in situ by means of the polymerization initiator after the polymerizable promoter is placed in contact with the substrate.

The polymerizable promoter is preferably included in the primer in an amount in a range from about 0.05% to about 99.95% by weight of the primer. The polymerizable promoter is more preferably included in an amount in a range from about 0.5% to about 50% by weight of the primer and most preferably in an amount in a range from about 0.75% to about 30% by weight of the primer.

The preferred polymerizable promoter is methacrylic acid which is also known as 2-methyl-2-propenoic acid. Other polymerizable promoters within the scope of the present invention typically have the following formula:

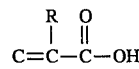

wherein R is a hydrogen atom, a methyl group, a saturated aliphatic radical, an unsaturated aliphatic radical, a halogen or a CN radical.

Additionally, polymerizable promoters within the scope of the present invention can also have the following formula:

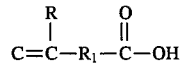

wherein R is a hydrogen atom, a methyl group, a saturated aliphatic radical, an unsaturated aliphatic radical, a halogen or a CN radical; and wherein $R_1$, is at least one oxygen atom, a saturated aliphatic radical, a saturated aliphatic radical interrupted by at least one oxygen atom, an unsaturated aliphatic radical, an unsaturated aliphatic radical interrupted by at least one oxygen atom, a homocyclic radical, a heterocyclic radical, a polymerizable moiety, or an aryl radical having four to six carbon atoms and a valency of n+1 with n being an integer of at least 6. Such polymerizable promoters include but are not limited to 4-pentenoic acid, 6-heptenoic acid and 2,2-dimethyl-4-pentenoic acid.

The polymerization initiator is selected from the group consisting of photoinitiators and chemical initiators. Photoinitiators include, but are not limited to, α-diketones with or without tertiary amines, such as camphoroquinone, dimethylamino ethylmethacrylate, and the like. Photoinitiators are the preferred polymerization initiators and camphoroquinone is the preferred photoinitiator. Chemical initiators may also be used in the primer either alone or as incorporated into the appropriate bonding resin to follow. The polymerization initiator is preferably included in the primer in an amount in a range from about 0.01% to about 2% by weight of the primer. The polymerization initiator is more preferably included in the primer in an amount in a range from about 0.03% to about 1.5% by weight of the primer, and most preferably included in the primer in an amount in a range from about 0.05% to about 1% by weight of the primer.

The primer may further comprise polymerizable resins. The term "polymerizable resin" as used in the specification and the appended claims refers to a either a hydrophilic polymerizable compound with at least one hydroxyl group, a hydrophobic polymerizable alkyl, or a polymerizable compound having at least one hydrophobic moiety and at least one hydrophilic moiety. Polymerizable resins within the scope of the present invention include hydroxyalkyl methacrylates, hydroxyalkyl acrylates, alkyl methacrylates, or alkyl acrylates. Particularly useful examples of the above polymerizable resins within the scope of the invention include 2-hydroxyethyl methacrylate (HEMA), bisphenol-A-glycidyl methacrylate, glycerol dimethacrylate, methyl acrylate, triethylene glycol dimethacrylate and the like. It is preferable to use hydrophilic resins such as HEMA, as the dentin contains significant moisture, which results in better adhesion between the dentin and the primer. Polymerizable resins within the scope of the present invention may also have at least one phosphate group and/or at least one amine group.

The polymerizable resin is preferably included in the primer in an amount in a range from about 0.05% to about 95% by weight of the primer. The polymerizable resin is more preferably included in the primer in an amount in a range from about 0.5% to about 80% by weight of the primer and most preferably included in the primer in an amount in a range from about 0.75% to about 70% by weight of the primer.

The primer may further comprise a solvent selected from the group consisting of a hydrophilic hydrocarbons, hydrophobic hydrocarbons, and water. The solvent imparts a desirable viscosity to the primer, which may increase the ability of the primer to flow into the intimate spaces afforded by selectively removing mineral components of dentin as per the conditioning (etching or chelating step). The solvent improves the ability of dentin bonding promoter(s) to make more intimate contact and impregnate into the conditioned dentin surface. The hydrophilic solvents are particularly useful since normal dentin is naturally moist.

Examples of suitable solvents include ethanol and acetone. The solvent is preferably included in the primer in an amount in a range from about 0.05% to about 95% by weight of the primer. The solvent is more preferably included in the primer in an amount in a range from about 0.5% to about 80% by weight of the primer, and most preferably included in the primer in an amount in a range from about 0.75% to about 50% by weight of the primer. The preferred solvent is ethanol. The solvent may be used in a primer comprising only a polymerizable promoter and a polymerization initiator. The solvent may also be combined with a polymerizable promoter, a polymerization initiator, and a polymerizable resin.

A natural resin may also be included in the primer. The term "natural resin" as used in the specification and the appended claims includes resins, distillates, saps, oils, balsams, or gums that come from natural sources such as trees, shrubs, plants or seeds. Any natural resin is within the scope of the present invention particularly those selected from the group consisting of Canadian balsam, sandarac, mastic, pontianak, copal, rosin, manilia, peruvian, benzoin, elemi, opopanax, olibanum, styrax, benzoin siam, tolu, tall, pine and the like. Mixtures of various natural resins can also be incorporated into the primer. Natural resins within the scope of the present invention include natural resins which are either polymerizable or non-polymerizable. Additionally, natural resins within the scope of the present invention either enhance the bond strength between a substrate primed with a primer containing such natural resins and a subsequently applied bonding material or do not in a significant manner adversely effect the bond strength. It is within the scope of the present invention to combine any of these natural resins with any conventional dentin primer bonding systems.

One of ordinary skill in the art would not expect to obtain a high bond strength between a polymerizable dental resin and a primer containing a natural resin as it has been well known since the advent of polymerizable dental materials that such materials adjacent to natural resins, such as copal rosin or copalite varnish, do not polymerize or harden. It is also known that Eugenol, which is derived from oil of cloves, can adversely effect polymerization of resinous dental materials.

Temporary cements are useful to retain a temporary crown in place. Temporary cements are weak so they can easily be removed when the permanent crown is ready for permanent placement. Eugenol in temporary cements can prevent complete polymerization of polymerizable dental resins such as methyl methacrylate, Bis-GMA and the like. Additionally, plastic crowns which have already been polymerized and are then placed in contact with a temporary cement containing Eugenol are softened by the Eugenol. It is also known that the Eugenol containing temporary cements must be completely removed from the tooth preparation before a polymerizable dental resin is applied as residual amounts of the Eugenol have an adverse effect on the ability of a polymerizable dental resin to polymerize and bond. Surprisingly, primers of the present invention are not as sensitive to residual Eugenol. It has been found that residual Eugenol does not adversely effect the bond strength when an appropriate resin material is applied after the dentin has been primed with a primer of the present invention.

In summary, the adverse effect of Eugenol and copal rosin on polymerizable dental resins would not suggest that a significant bond would result between a polymerizable dental resin and dentin primed with a primer containing a natural resin or that the polymerizable dental resin would effectively polymerize It is also surprising that polymerization is effectively achieved of polymerizable components intermixed with natural resins in the polymerizable primer of the present invention. Additionally, since the exact small quantity chemical content of each natural resins is not known, one of ordinary skill in the art would not expect to obtain a highly stable system by incorporating such a natural resin in a polymerizable composition.

The natural resin is preferably included in the primer in an amount in a range from about 0.05% to about 55% by weight of the primer. The natural resin is more preferably included in the primer in an amount in a range from about 0.5% to about 35% by weight of the primer, and most preferably included in the primer in an amount in a range from about 0.75% to about 20% by weight of the primer.

It is within the scope of the present invention to form primers comprising at least one polymerizable promoter, at least one natural resin, at least one solvent and at least one polymerization initiator. It is also within the scope of the present invention to form primers comprising at least one polymerizable promoter, at least one natural resin, at least one polymerizable resin and at least one polymerization initiator.

The preferred embodiment comprises at least one polymerizable promoter, at least one natural resin, at least one hydrophilic polymerizable resin, at least one solvent and at least one polymerization photoinitiator and a chemical initiator. In some cases it is desirable to include a chemical initiator since in all circumstances light cannot appropriately reach the application site to cause complete polymerization or cannot address polymerization in a desired direction. In the most preferred embodiment the polymerizable promoter is methacrylic acid, the natural resin is Canadian balsam, the polymerizable resin is 2-hydroxyethyl methacrylate (HEMA), the solvent is ethanol and the polymerization initiator is camphoroquinone. By weight of the primer, the composition of the most preferred embodiment comprises about 6% methacrylic acid, about 15% Canadian balsam, about 53.3% 2-hydroxyethyl methacrylate, about 25% ethanol and about 0.7% camphoroquinone.

In two alternative embodiments, the polymerizable component is a polymerizable resin and not a polymerizable promoter. In one of the embodiments, the primer comprises a natural resin, a polymerizable resin and a polymerization initiator. In the other alternative embodiment, the primer comprises a natural resin, a polymerizable resin, a solvent and a polymerization initiator.

It is currently believed that the components of the dentin bonding promoter have hydrophilic moieties, particularly the carboxylic acid groups of the polymerizable promoters, which tend to interact with the hydrophilic surface of the dentin, while the more hydrophobic moieties tend to orient themselves outward, creating a much more hydrophobic surface with which the resinous materials can interact. Regardless of the actual mechanism involved, greatly improved bond strengths have been demonstrated. In fact, the bond strengths are usually stronger than the dentin itself, which results in test fractures occurring within the dentin instead of the bond between the dentin and resinous material.

The dentin primers of the present invention yield bond strengths between about 15–35 MPa depending on the protocol of individual laboratories. In addition to superior bond strengths compared to dentin bonding agents available on the market today, the dentin primers of the present invention have a relatively long shelf life and do not require multiple coatings.

EXAMPLES OF THE PREFERRED EMBODIMENTS

Examples are provided of the present invention in order to compare the properties of the compositions by varying the content of the components of the dentin primer. Examples 1–13 describe dentin primers which were prepared in accordance with the present invention. Examples 14–18 described dentin primers which can be hypothetical prepared based on actual mix designs in accordance with the present invention. While examples 14–18 are hypothetical in nature, they are based upon actual mix designs that have been tested or contemplated and are presented in this form in order to more completely illustrate the nature of the invention.

Example 1

A dentin primer was formed from the following components:

| Component | Percent by Weight of the Mixture |
| --- | --- |
| Methacrylic Acid | 6.0 |
| Canadian Balsam | 15.0 |
| HEMA | 53.3 |
| Ethanol | 25.0 |
| Camphoroquinone | 0.7 |

Dentin was etched with a phosphoric acid solution having a concentration of about 35%. The etched dentin was flushed away with water and then the dentin was dried by air.

After the dentin primer was prepared, it was placed in a syringe assembly and delivered onto the dentin which had been etched, rinsed and dried. The viscosity of the dentin primer was low enough that the dentin primer sufficiently flowed into the micro spaces of the conditioned dentin. Polymerization was achieved by exposing the primer to light. The dentin primer had a pH which was almost neutral. The dentin primer adequately adhered to the tooth surface where it was applied. A resin material was applied and the strength of the resulting bond was most significant as it was very high. The process was repeated and it was found that the process was repeatable in approximately equal time periods and that the bond strengths were approximately equal.

Example 2

A dentin primer was formed from the following components:

| Component | Percent by Weight of the Mixture |
| --- | --- |
| Methacrylic Acid | 6.0 |
| Canadian Balsam | 15.0 |
| HEMA | 53.3 |
| Bisphenol-A-glycidyl methacrylate | 5.0 |
| Ethanol | 20.0 |
| Camphoroquinone | 0.7 |

Dentin was etched with a phosphoric acid solution having a concentration of about 35%. The etched dentin was flushed away with water and then the dentin was dried by air.

After the dentin primer was prepared, it was placed in a syringe assembly and delivered onto the dentin which had been etched, rinsed and dried. The viscosity of the dentin primer was very similar to the viscosity in Example 1 and was low enough that the dentin primer sufficiently flowed into the micro spaces of the conditioned dentin. Polymerization was achieved by exposing the primer to light. The dentin primer had a pH which was almost neutral. The dentin primer adhered to the tooth surface where it was applied and formed a bond with a resin material applied onto the primer which had a strength approximately equal to the bond strengths achieved in Example 1 when resin material was applied to the primer.

Example

A dentin primer was formed from the following components:

| Component | Percent by Weight of the Primer |
| --- | --- |
| Methacrylic acid | 6 |
| HEMA | 52.6 |
| Canadian balsam | 15 |
| Ethanol | 25.4 |
| Benzoyl Peroxide | 1 |

The composition of this primer behaved similarly to the composition of the primer prepared in Example 1. The polymerization initiator in this composition was a chemical initiator. The chemical initiator, benzoyl peroxide, adequately initiated polymerization when contacted with an aromatic amine accelerator in the resinous material.

Example 4

A dentin primer was formed from the following components:

| Component | Percent by Weight of the Primer |
| --- | --- |
| Methacrylic acid | 7 |
| Canadian balsam | 15 |
| HEMA | 47.5 |
| Ethanol | 25 |
| Acetone | 4 |
| Camphoroquinone | 0.6 |
| 2,2'p-tolyimino diethanol | 0.9 |

The composition of this primer was nearly identical to composition of the primer prepared in Example 1, except that acetone was also included as a solvent and polymerization was initiated by a photoinitiator and a chemical initiator. The use of ethanol and acetone together as a solvent was less effective than using ethanol alone. The chemical initiator, 2,2'p-tolyimino diethanol, adequately initiated polymerization when contacted with a free radical initiator in the resinous material.

Example 5

A dentin primer was formed from the following components:

| Component | Percent by Weight of the Primer |
| --- | --- |
| Methacrylic acid | 0.5 |
| HEMA | 62.9 |
| Canadian balsam | 15 |
| Ethanol | 20.4 |
| Camphoroquinone | 0.7 |
| Benzoyl peroxide | 0.5 |

Polymerization was adequately initiated by the combined use of a photoinitiator and a chemical initiator. The dentin was adequately covered and the bond strength was significant but weaker than the bond strength achieved with the composition in Example 1.

Example 6

A dentin primer was formed from the following components:

| Component | Percent by Weight of the Primer |
| --- | --- |
| Methacrylic acid | 6.4 |
| HEMA | 52.9 |
| Ethanol | 40 |
| Camphoroquinone | 0.7 |

This dentin primer was prepared without any natural resins and a larger amount of solvent than the dentin primer prepared in Example 1. The primer was easily covered with the primer which had a lower viscosity than the primer in Example 1. The bond was significant but somewhat weaker compared to the bond formed in Example 1.

Example 7

A dentin primer was formed from the following components:

| Component | Percent by Weight of the Primer |
|---|---|
| Methacrylic Acid | 10.0 |
| Ethanol | 89.3 |
| Camphoroquinone | 0.7 |

The solvent content was very high and was prepared without any natural resins or polymerizable resins. The primer easily flowed since it had a very low viscosity, however, more drying was necessary than in Example 1. Significant bond strengths were obtained after multiple coats were applied.

Example 8

A dentin primer was formed from the following components:

| Component | Percent by Weight of the Primer |
|---|---|
| Methacrylic acid | 6.4 |
| HEMA | 77.9 |
| Sandarac resin | 15 |
| Camphoroquinone | 0.7 |

The viscosity of the dentin primer was much higher than in Example 1 as there was no solvent and the HEMA content was much higher. More air blowing was necessary to spread and thin the primer than was necessary in Example 1, however, the primer sufficiently infiltrated the conditioned dentin. The bond strength was significant but not as high as in Example 1.

Example 9

A dentin primer was formed from the following components:

| Component | Percent by Weight of the Primer |
|---|---|
| HEMA | 80 |
| Mastic resin | 19.5 |
| Camphoroquinone | 0.5 |

The viscosity of the dentin primer was much higher than in Example 1 as there was no solvent and the resin content was 99.5% of the primer. Much more air blowing was necessary to spread and thin the primer than was necessary in Example 1, however, sufficient contact was achieved between the primer and the dentin. The bond strength was significant but not as high as in Example 1.

Example 10

A dentin primer was formed from the following components:

| Component | Percent by Weight of the Primer |
|---|---|
| Methacrylic acid | 2 |
| HEMA | 76.8 |
| Bisphenol-A-glycidyl methacrylate | 3.9 |
| Pontianak resin | 16 |
| Ethanol | 5 |
| Camphoroquinone | 0.8 |

Due to the low solvent content, the viscosity of the dentin primer was relatively high and resulted in the need for more air blowing to adequately spread and thin the primer than was necessary in Example 1. The strength of the bond was significant but weaker than the bond formed by the primer of Example 1.

Example 11

A dentin primer was formed from the following components:

| Component | Percent by Weight of the Primer |
|---|---|
| Methacrylic acid | 3 |
| HEMA | 84.1 |
| Copal gum | 12 |
| Camphoroquinone | 0.9 |

The viscosity of the dentin primer was much higher than in Example 1 as there was no solvent, however, significant impregnation was achieved by the primer into the dentin. The bond strength was quite significant.

Example 12

A dentin primer was formed from the following components:

| Component | Percent by Weight of the Primer |
|---|---|
| Methacrylic acid | 6 |
| HEMA | 52.6 |
| Olibanum resin | 15.4 |
| Ethanol | 25 |
| 2,2'p-tolylimino diethanol | 1 |

The viscosity of the dentin primer was very similar to the viscosity of the primer described in Example 1. Polymerization was adequately achieved by the chemical initiator, 2,2'p-tolylimino diethanol, but was not as effective as camphoroquinone. The bond had significant strength but was weaker than in Example 1.

Example 13

A dentin primer was formed from the following components:

| Component | Percent by Weight of the Mixture |
|---|---|
| Methacrylic Acid | 6.0 |
| Canadian Balsam | 15.0 |
| Maleic Acid | 0.3 |
| HEMA | 53.0 |
| Ethanol | 25.0 |
| Camphoroquinone | 0.7 |

The dentin primer had an acidic pH, however, the strength of the bond formed when a resin material was applied was very near the level of the bond strengths achieved by the composition in Example 1.

Example 14

A dentin primer is formed from the following components:

| Component | Percent by Weight of the Primer |
|---|---|
| Methacrylic acid | 2 |
| HEMA | 30 |
| Canadian balsam | 31 |
| Ethanol | 35.8 |
| Camphoroquinone | 1.2 |

A dentin primer prepared by the above composition would be expected to have a significant bond strength but weaker than the bond formed in Example 1. The primer would also be expected to be slightly less viscous than the primer prepared in Example 1 which would not vary the process.

Example 15

A dentin primer is formed from the following components:

| Component | Percent by Weight of the Primer |
|---|---|
| Methacrylic acid | 8 |
| HEMA | 91.1 |
| Camphoroquinone | 0.9 |

A dentin primer prepared by the above composition would be expected to have a significant bond strength but lower than in Example 1. Additionally, the dentin primer would be expected to be very viscous as no solvent is used and the HEMA content is very high. Much more air blowing would be necessary to spread the relatively viscous mixture.

Example 16

A dentin primer is formed from the following components:

| Component | Percent by Weight of the Primer |
|---|---|
| Methacrylic acid | 99.3 |
| Camphoroquinone | 0.7 |

A dentin primer prepared by the above composition would be expected to have a significant bond strength but weaker than the bond formed in Example 1. The viscosity would be low since methacrylic acid has a low viscosity. The dentin primer formed in accordance with the above composition would be expected to provide a bond strength having significant but less than Example 1.

Example 17

A dentin primer is formed from the following components:

| Component | Percent by Weight of the Primer |
|---|---|
| Methacrylic acid | 9 |
| Tolu balsam | 19 |
| Camphoroquinone | 0.6 |
| Ethanol | 71.4 |

A dentin primer prepared by the above composition would be expected to have a low viscosity due to the high amount of solvent allowing the primer to easily cover the dentin, however, multiple coats may be necessary to obtain significant bonding. Although, the bond between a subsequently applied appropriate resin material and the primer would be expected to be significant, it would also be expected to be lower than the bond formed in Example 1.

Example 18

A dentin primer is formed from the following components:

| Component | Percent by Weight of the Primer |
|---|---|
| HEMA | 13 |
| Camphoroquinone | 1.2 |
| Ethanol | 76.3 |
| Manila resin | 20 |

A dentin primer prepared by the above composition would be expected to have a very low viscosity due to the high amount of solvent allowing the primer to easily cover the dentin, however, multiple coats may be necessary to obtain significant bonding. Although, the bond between a subsequently applied appropriate resin material and the primer would be expected to be significant, it would also be expected to be lower than the bond formed in Example 1.

SUMMARY

From the foregoing, it will be appreciated that the present invention provides novel compositions for a dentin primer and methods for priming dentin.

In particular, the present invention provides dental compositions and methods for more efficiently obtaining stronger, more predictable bonds between dentin and subsequently placed resinous materials. It will also be appreciated that an object of the present invention is to provide compositions having a long shelf life which would result in dependable bonds over time during storage and usage.

The present invention also provides dental compositions and methods which are more simple to use than in the prior art by providing a dentin primer which is stable as a one component system and more stable than all types of existing dentin primers.

The present invention further provides compositions and methods for sealing a biological substrate without interfering with the bond achieved with a material which is thereafter applied such as glass ionomer cement or polycarboxylate cements.

Further, the present invention provides compositions and methods for a single component primer which has an approximately neutral pH level.

Finally, the present invention provides compositions and methods for obtaining significant bonding strengths with an appropriately conditioned enamel, porcelain, metal, or composite surface(s) when followed by an appropriate bonding resin.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A stable premixed primer for sealing or priming for bonding a dental substrate or a biological substrate, the stable premixed primer comprising:
   a polymerization initiator; and
   a polymerizable promoter characterized as being capable of being polymerized in situ by initiation of the polymerization initiator after the primer is placed in contact with the substrate, wherein the polymerizable promoter is selected from the group consisting of methacrylic acid, 4-pentenoic acid, 6-heptenoic acid and 2,2-dimethyl-4-pentenoic acid, and wherein the polymerizable initiator and the polymerizable promoter once mixed thereafter form a stable premixed primer ready for storage and subsequent application directly to the substrate without additional mixing.

2. A primer as defined in claim 1, wherein the polymerizable promoter has a concentration in a range from about 0.5% to about 50% by weight of the primer.

3. A primer as defined in claim 1, wherein the polymerizable promoter has a concentration in a range from about 0.75% to about 30% by weight of the primer.

4. A primer as defined in claim 1, wherein the polymerization initiator has a concentration in a range from about 0.01% to about 2% by weight of the primer.

5. A primer as defined in claim 1, wherein the polymerization initiator has a concentration in a range from about 0.03% to about 1.5% by weight of the primer.

6. A primer as defined in claim 1, wherein the polymerization initiator has a concentration in a range from about 0.05% to about 1% by weight of the primer.

7. A primer as defined in claim 1, wherein the polymerization initiator is a photoinitiator.

8. A primer as defined in claim 1, wherein the polymerization initiator is a chemical initiator.

9. A primer as defined in claim 1, further comprising a polymerizable resin.

10. A primer as defined in claim 1, further comprising a hydrophilic polymerizable resin having at least one hydroxy group.

11. A primer as defined in claim 1, further comprising a hydrophobic polymerizable alkyl resin.

12. A primer as defined in claim 9, wherein the polymerizable resin is selected from the group consisting of a hydroxyalkyl methacrylate, a hydroxyalkyl acrylate, an alkyl methacrylate, an alkyl acrylate, and mixtures thereof.

13. A primer as defined in claim 9, wherein the polymerizable resin is selected from the group consisting of 2-hydroxyethyl methacrylate, bisphenol-A-glycidyl methacrylate, glycerol dimethacrylate, methyl acrylate, and triethyleneglycol dimethacrylate.

14. A primer as defined in claim 9, wherein the polymerizable resin has at least one phosphate group.

15. A primer as defined in claim 9, wherein the polymerizable resin has at least one amine group.

16. A primer as defined in claim 9, wherein the polymerizable resin has a concentration in a range from about 0.05% to about 95% by weight of the primer.

17. A primer as defined in claim 9, wherein the polymerizable resin has a concentration in a range from about 0.5% to about 80% by weight of the primer.

18. A primer as defined in claim 9, wherein the polymerizable resin has a concentration in a range from about 0.75% to about 70% by weight of the primer.

19. A primer as defined in claim 1, further comprising a solvent.

20. A primer as defined in claim 19, wherein the solvent is selected from the group consisting of a hydrophilic hydrocarbon, a hydrophobic hydrocarbon and water.

21. A primer as defined in claim 19, wherein the solvent is ethanol.

22. A primer as defined in claim 19, wherein the solvent is acetone.

23. A primer as defined in claim 19, wherein the solvent has a concentration in a range from about 0.05% to about 95% by weight of the primer.

24. A primer as defined in claim 19, wherein the solvent has a concentration in a range from about 0.5% to about 80% by weight of the primer.

25. A primer as defined in claim 19, wherein the solvent has a concentration in a range from about 0.75% to about 50% by weight of the primer.

26. A primer as defined in claim 1, further comprising a natural resin.

27. A primer as defined in claim 26, wherein the natural resin is derived from natural sources and is selected from the group consisting of a rosin, a distillate, a sap, an oil, a balsam, a gum, and mixtures thereof.

28. A primer as defined in claim 26, wherein the natural resin is selected from the group consisting of Canadian balsam, sandarac, mastic, pontianak, copal, manilla, peruvian, benzoin, elemi, opopanax, olibanum, styrax, benzoin siam, tolu, tall, pine, and mixtures thereof.

29. A primer as defined in claim 26, wherein the natural resin has a concentration in a range from about 0.05% to about 55% by weight of the primer.

30. A primer as defined in claim 26, wherein the natural resin has a concentration in a range from about 0.5% to about 35% by weight of the primer.

31. A primer as defined in claim 26, wherein the natural resin has a concentration in a range from about 0.75% to about 20% by weight of the primer.

32. A stable premixed primer for sealing or priming for bonding a dental substrate or a biological substrate, the stable premixed primer comprising:
   a polymerization initiator;
   a solvent; and
   a polymerizable promoter characterized as being capable of being polymerized in situ by initiation of the polymerization initiator after the primer is placed in contact with the substrate, wherein the polymerizable promoter is selected from the group consisting of methacrylic acid, 4-pentenoic acid, 6-heptenoic acid and 2,2-dimethyl-4-pentenoic acid, and wherein the polymerizable initiator, solvent and the polymerizable promoter once mixed thereafter form a stable premixed primer ready for storage and subsequent application directly to the substrate without additional mixing.

33. A primer as defined in claim 32, wherein the solvent is selected from the group consisting of a hydrophilic hydrocarbon, a hydrophobic hydrocarbon and water.

34. A primer as defined in claim 32, wherein the solvent is ethanol.

35. A primer as defined in claim 32, wherein the solvent is acetone.

36. A primer as defined in claim 32, further comprising a polymerizable resin.

37. A primer as defined in claim 37, further comprising a hydrophilic polymerizable resin having at least one hydroxy group.

38. A primer as defined in claim 32, further comprising a hydrophobic polymerizable alkyl resin.

39. A primer as defined in claim 32, further comprising a polymerizable resin selected from the group consisting of a hydroxyalkyl methacrylate, a hydroxyalkyl acrylate, an alkyl methacrylate, an alkyl acrylate, and mixtures thereof.

40. A primer as defined in claim 32, further comprising a polymerizable resin selected from the group consisting of 2-hydroxyethyl methacrylate, bisphenol-A-glycidyl methacrylate, glycerol dimethacrylate, methyl acrylate, and triethyleneglycol dimethacrylate.

41. A primer as defined in claim 36, wherein the polymerizable resin has at least one phosphate group.

42. A primer as defined in claim 36, wherein the polymerizable resin has at least one amine group.

43. A primer as defined in claim 32, further comprising a natural resin.

44. A primer as defined in claim 32, wherein the natural resin is derived from natural sources and is selected from the group consisting of a rosin, a distillate, a sap, an oil, a balsam, a gum, and mixtures thereof.

45. A primer as defined in claim 32, further comprising a natural resin selected from the group consisting of Canadian balsam, sandarac, mastic, pontianak, copal, manilla, peruvian, benzoin, elemi, opopanax, olibanum, styrax, benzoin siam, tolu, tall, pine, and mixtures thereof.

46. A premixed primer for sealing or priming for bonding a dental substrate or a biological substrate, the stable premixed primer comprising:

a polymerization initiator;

a polymerizable resin; and a polymerizable promoter characterized as being capable of being polymerized in situ by initiation of the polymerization initiator after the primer is placed in contact with the substrate, wherein the polymerizable promoter is selected from the group consisting of methacrylic acid, 4-pentenoic acid, 6-heptenoic acid and 2,2-dimethyl-4-pentenoic acid, and wherein the polymerizable initiator, polymerizable resin and the polymerizable promoter once mixed thereafter form a stable premixed primer ready for storage and subsequent application directly to the substrate without additional mixing.

47. A primer as defined in claim 46, wherein the polymerizable resin is hydrophilic and has at least one hydroxy group.

48. A primer as defined in claim 46, wherein the polymerizable resin is a hydrophobic polymerizable alkyl resin.

49. A primer as defined in claim 46, wherein the polymerizable resin is selected from the group consisting of a hydroxyalkyl methacrylate, a hydroxyalkyl acrylate, an alkyl methacrylate, an alkyl acrylate, and mixtures thereof.

50. A primer as defined in claim 46, wherein the polymerizable resin is selected from the group consisting of 2-hydroxyethyl methacrylate, bisphenol-A-glycidyl methacrylate, glycerol dimethacrylate, methyl acrylate, and triethyleneglycol dimethacrylate.

51. A primer as defined in claim 46, wherein the polymerizable resin has at least one phosphate group.

52. A primer as defined in claim 46, wherein the polymerizable resin has at least one amine group.

53. A primer as defined in claim 46, further comprising a solvent selected from the group consisting of a hydrophilic hydrocarbon, a hydrophobic hydrocarbon and water.

54. A primer as defined in claim 46, further comprising ethanol.

55. A primer as defined in claim 46, further comprising acetone.

56. A primer as defined in claim 46, further comprising a natural resin.

57. A primer as defined in claim 46, wherein the natural resin is derived from natural sources and is selected from the group consisting of a rosin, a distillate, a sap, an oil, a balsam, a gum, and mixtures thereof.

58. A primer as defined in claim 46, further comprising a natural resin selected from the group consisting of Canadian balsam, sandarac, mastic, pontianak, copal, manilla, peruvian, benzoin, elemi, opopanax, olibanum, styrax, benzoin siam, tolu, tall, pine and mixtures thereof.

59. A primer for sealing or priming for bonding a dental or a biological substrate, the primer comprising:

a polymerization initiator;

a natural resin; and a polymerizable promoter characterized as being capable of being polymerized in situ by initiation of the polymerization initiator alter the primer is placed in contact with the substrate, the polymerizable promoter comprising at least one polymerizable prepolymer having at least one ethylenically unsaturated group and at least one carboxylic acid group.

60. A primer as defined in claim 59, wherein the polymerizable promoter has the following formula:

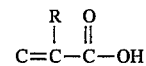

wherein R is a hydrogen atom, a methyl group, a saturated aliphatic radical, an unsaturated aliphatic radical, a halogen or a CN radical.

61. A primer as defined in claim 59, wherein the polymerizable promoter has the following formula:

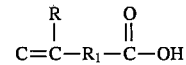

wherein R is a hydrogen atom, a methyl group, a saturated aliphatic radical, an unsaturated aliphatic radical, a halogen or a CN radical; and wherein $R_1$ is at least one oxygen atom, a saturated aliphatic radical, a saturated aliphatic radical interrupted by at least one oxygen atom, an unsaturated aliphatic radical, an unsaturated aliphatic radical interrupted by at least one oxygen atom, a homocyclic radical, a heterocyclic radical, a polymerizable moiety, or an aryl radical having four to six carbon atoms and a valency of n+1 with n being an integer of at least 6.

62. A primer as defined in claim 59, wherein the polymerizable promoter is methacrylic acid.

63. A primer as defined in claim 59, wherein the polymerizable promoter is selected from the group consisting of 4-pentenoic acid, 6-heptenoic acid and 2,2-dimethyl-4-pentenoic acid.

64. A primer as defined in claim 59, wherein the natural resin is derived from natural sources and is selected from the group consisting of a rosin, a distillate, a sap, an oil, a balsam, a gum, and mixtures thereof.

65. A primer as defined in claim 59, wherein the natural resin is selected from the group consisting of Canadian balsam, sandarac, mastic, pontianak, copal, manilla, peruvian, benzoin, elemi, opopanax, olibanum, styrax, benzoin siam, tolu, tall, pine, and mixtures thereof.

66. A primer as defined in claim 59, further comprising a hydrophilic polymerizable resin having at least one hydroxy group.

67. A primer as defined in claim 59, further comprising a hydrophobic polymerizable alkyl resin.

68. A primer as defined in claim 59, further comprising a polymerizable resin selected from the group consisting of a hydroxyalkyl methacrylate, a hydroxyalkyl acrylate, an alkyl methacrylate, an alkyl acrylate, and mixtures thereof.

69. A primer as defined in claim 59, further comprising a polymerizable resin selected from the group consisting of 2-hydroxyethyl methacrylate, bisphenol-A-glycidyl methacrylate, glycerol dimethacrylate, methyl acrylate, and triethyleneglycol dimethacrylate.

70. A primer as defined in claim 59, further comprising a polymerizable resin having at least one phosphate group.

71. A primer as defined in claim 59, further comprising a polymerizable resin having at least one amine group.

72. A primer as defined in claim 59, further comprising a solvent selected from the group consisting of a hydrophilic hydrocarbon, a hydrophobic hydrocarbon and water.

73. A primer as defined in claim 59, further comprising ethanol.

74. A primer as defined in claim 59, further comprising acetone.

75. A primer for sealing or printing for bonding a dental or a biological substrate, the primer comprising:

a polymerization initiator;

a natural resin; and a polymerizable resin.

76. A primer as defined in claim 75, wherein the natural resin is derived from natural sources and is selected from the group consisting of a rosin, a distillate, a sap, an oil, a balsam, a gum, and mixtures thereof.

77. A primer as defined in claim 75, wherein the natural resin is selected from the group consisting of Canadian balsam, sandarac, mastic, pontianak, copal, manilla, peruvian, benzoin, elemi, opopanax, olibanum, styrax, benzoin siam, tolu, tall, pine, and mixtures thereof.

78. A primer as defined in claim 75, wherein the polymerizable resin is hydrophilic and has at least one hydroxy group.

79. A primer as defined in claim 75, wherein the polymerizable resin is a hydrophobic polymerizable alkyl resin.

80. A primer as defined in claim 75, wherein the polymerizable resin is selected from the group consisting of a hydroxyalkyl methacrylate, a hydroxyalkyl acrylate, an alkyl methacrylate, an alkyl acrylate, and mixtures thereof.

81. A primer as defined in claim 75, wherein the polymerizable resin is selected from the group consisting of 2-hydroxyethyl methacrylate, bisphenol-A-glycidyl methacrylate, glycerol dimethacrylate, methyl acrylate, and triethyleneglycol dimethacrylate.

82. A primer as defined in claim 75, wherein the polymerizable resin has at least one phosphate group.

83. A primer as defined in claim 75, wherein the polymerizable resin has at least one amine group.

84. A primer as defined in claim 75, further comprising a solvent selected from the group consisting of a hydrophilic hydrocarbon, a hydrophobic hydrocarbon and water.

85. A primer as defined in claim 75, further comprising ethanol.

86. A primer as defined in claim 75, further comprising acetone.

87. A primer for sealing or priming for bonding a dental or a biological substrate, the primer comprising methacrylic acid, Canadian balsam, 2-hydroxyethyl methacrylate, ethanol and camphoroquinone.

88. A primer for sealing or printing for bonding a dental or a biological substrate, the primer comprising about 6% methacrylic acid by weight of the primer, about 15% Canadian balsam by weight of the primer, about 53.3% 2-hydroxyethyl methacrylate by weight of the primer, about 25% ethanol by weight of the primer and about 0.7% camphoroquinone by weight of the primer.

89. A method for preparing a stable premixed primer for sealing or priming for bonding a dental or a biological substrate, comprising the step of mixing a polymerization initiator with a polymerizable promoter to form a stable premixed primer ready for storage and subsequent application directly to a substrate without additional mixing, wherein the polymerizable promoter is characterized as being capable of being polymerized in situ by initiation of the polymerization initiator after the stable premixed primer is placed in contact with the substrate and wherein the polymerizable promoter is selected from the group consisting of methacrylic acid, 4-pentenoic acid, 6-heptenoic acid and 2,2-dimethyl-4-pentenoic acid.

90. A method for preparing primer for sealing or priming for bonding a dental or biological substrate, comprising the step of mixing a natural resin, a polymerizable resin, and a polymerization initiator.

91. A method for priming for bonding or sealing a dental or biological substrate with a stable premixed primer comprising the steps of:

applying a stable premixed primer to the substrate, the stable premixed primer comprising a polymerization initiator and a polymerizable promoter, wherein the polymerizable promoter is characterized as being capable of being polymerized in situ by initiation of the polymerization initiator after the stable premixed primer is applied to the substrate, wherein the polymerizable promoter is selected from the group consisting of methacrylic acid, 4-pentenoic acid 6-heptenoic acid and 2,2-dimethyl-4-pentenoic acid, and wherein the premixed stable primer is characterized after being premixed as being ready for storage and subsequent application directly to a substrate without additional mixing; and initiating the polymerization of the polymerizable promoter.

92. A method for priming for bonding or sealing a dental or biological substrate with a primer comprising the steps of:

applying a primer to the substrate, the primer comprising a natural resin, a polymerizable resin, and a polymerization initiator; and initiating the polymerization of the polymerizable promoter.

93. A kit for priming for bonding or sealing a dental or biological substrate with a stable premixed primer comprising:

(a) a substrate conditioner; and (b) a stable premixed primer comprising a polymerization initiator and a polymerizable promoter, wherein the polymerizable promoter is characterized as being capable of being polymerized in situ by initiation of the polymerization initiator after the primer is applied to the substrate, wherein the polymerizable promoter is selected from the group consisting of methacrylic acid, 4-pentenoic acid, 6-heptenoic acid and 2,2-dimethyl-4-pentenoic acid, and wherein the polymerizable initiator and the polymerizable promoter once mixed thereafter form a stable premixed primer ready for storage and subsequent application directly to the substrate without additional mixing.

94. A kit as defined in claim 93, wherein the substrate conditioner is a grit blaster.

95. A kit as defined in claim 93, wherein the substrate conditioner is an acid etching solution.

96. A kit for priming for bonding or sealing a dental or biological substrate with a primer comprising:

(a) a substrate conditioner; and (b) a primer comprising a natural resin, a polymerizable resin, and a polymerization initiator.

97. A kit as defined in claim 96, wherein the substrate conditioner is a grit blaster.

98. A kit as defined in claim 96, wherein the substrate conditioner is an acid etching solution.

99. A method for preparing a stable premixed primer for sealing or priming for bonding a dental or biological substrate, comprising the step of mixing a polymerization initiator, a polymerizable resin, and a polymerization promoter to form a stable premixed primer ready for storage and subsequent application directly to the substrate without additional mixing, wherein the polymerizable promoter is characterized as being capable of being polymerized in situ by initiation of the polymerization initiator after the stable premixed primer is applied to the substrate and wherein the polymerizable promoter is selected from the group consisting of methacrylic acid, 4-pentenoic acid, 6-heptenoic acid and 2,2-dimethyl-4-pentenoic acid.

100. A method for priming for bonding or sealing a dental or biological substrate with a stable premixed primer comprising the steps of:

applying a stable premixed primer to the substrate, the stable premixed primer comprising a polymerization initiator, a polymerizable resin and a polymerizable promoter, wherein the polymerizable promoter is characterized as being capable of being polymerized in situ by initiation of the polymerization initiator after the stable premixed primer is applied to the substrate, wherein the polymerizable promoter is selected from the group consisting of methacrylic acid, 4-pentenoic acid, 6-heptenoic acid and 2,2-dimethyl-4 -pentenoic acid, and wherein the premixed stable primer is characterized after being premixed as being ready for storage and subsequent application directly to a substrate without additional mixing; and initiating the polymerization of the polymerizable resin and the polymerizable promoter.

101. A method for preparing a primer for sealing or priming for bonding a dental or biological substrate, comprising the step of mixing a polymerization initiator, a natural resin, and a polymerization promoter to form a primer, wherein the polymerizable promoter is characterized as being capable of being polymerized in situ by initiation of the polymerization initiator after the primer is applied to the substrate and wherein the polymerizable promoter comprises at least one polymerizable prepolymer having at least one ethylenically unsaturated group and at least one carboxylic acid group.

102. A method for priming for bonding or sealing a dental or biological substrate with a primer comprising the steps of:

applying a primer to the substrate, the primer comprising a polymerization initiator, a natural resin and a polymerizable promoter, wherein the polymerizable promoter is characterized as being capable of being polymerized in situ by initiation of the polymerization initiator after the primer is applied to the substrate and wherein the polymerizable promoter comprises at least one polymerizable prepolymer having at least one ethylenically unsaturated group and at least one carboxylic acid group; and initiating the polymerization of the polymerizable promoter.

103. A kit for priming for bonding or sealing a dental or biological substrate with a primer comprising:

(a) a substrate conditioner; and (b) a stable premixed primer comprising a polymerization initiator, a polymerizable resin, a polymerizable promoter, wherein the polymerizable promoter is characterized as being capable of being polymerized in situ by initiation of the polymerization initiator after the stable premixed primer is applied to the substrate, wherein the polymerizable promoter is selected from the group consisting of methacrylic acid, 4-pentenoic acid, 6-heptenoic acid and 2,2-dimethyl-4-pentenoic acid and wherein the polymerizable initiator, polymerizable resin and the polymerizable promoter once mixed thereafter form a stable premixed primer ready for storage and subsequent application directly to the substrate without additional mixing.

104. A kit as defined in claim 103, wherein the substrate conditioner is a grit blaster.

105. A kit as defined in claim 103, wherein the substrate conditioner is an acid etching solution.

106. A kit for priming for bonding or sealing a dental or biological substrate with a primer comprising:

(a) a substrate conditioner; and (b) a primer comprising a polymerization initiator, a natural resin and a polymerizable promoter, wherein the polymerizable promoter is characterized as being capable of being polymerized in situ by initiation of the polymerization initiator after the primer is applied to the substrate and wherein the polymerizable promoter comprises at least one polymerizable prepolymer having at least one ethylenically unsaturated group and at least one carboxylic acid group.

107. A kit as defined in claim 106, wherein the substrate conditioner is a grit blaster.

108. A kit as defined in claim 106, wherein the substrate conditioner is an acid etching solution.

* * * * *